US009334521B2

(12) United States Patent
Robole et al.

(10) Patent No.: US 9,334,521 B2
(45) Date of Patent: May 10, 2016

(54) PROCESS CHALLENGE DEVICE AND METHODS

(75) Inventors: Barry W. Robole, Woodville, WI (US); William E. Foltz, Cottage Grove, MN (US)

(73) Assignee: 3m Innovative Properties Company, St. Paul, MN (US)

( * ) Notice: Subject to any disclaimer, the term of this patent is extended or adjusted under 35 U.S.C. 154(b) by 866 days.

(21) Appl. No.: 13/128,054

(22) PCT Filed: Nov. 5, 2009

(86) PCT No.: PCT/US2009/063330
§ 371 (c)(1),
(2), (4) Date: May 6, 2011

(87) PCT Pub. No.: WO2010/054033
PCT Pub. Date: May 14, 2010

(65) Prior Publication Data
US 2011/0217203 A1    Sep. 8, 2011

Related U.S. Application Data

(60) Provisional application No. 61/112,071, filed on Nov. 6, 2008.

(51) Int. Cl.
*A61L 2/18* (2006.01)
*G01N 1/00* (2006.01)
*G05D 16/00* (2006.01)
*C12Q 1/22* (2006.01)
*A61L 2/28* (2006.01)

(52) U.S. Cl.
CPC .... *C12Q 1/22* (2013.01); *A61L 2/28* (2013.01)

(58) Field of Classification Search
CPC ............... A61L 2/00; A61L 2/16; A61L 2/26; A61L 2/28; A61L 2202/00; A61L 2202/10; A61L 2202/12; A61L 2202/121
USPC .............................................. 422/3, 312, 430
See application file for complete search history.

(56) References Cited

U.S. PATENT DOCUMENTS 3,981,683 A     9/1976  Larsson et al.
4,115,068 A     9/1978  Joslyn et al.
(Continued)

FOREIGN PATENT DOCUMENTS

AU      2004224765 B2    10/2004
EP         0419282 A1     9/1990
(Continued)

OTHER PUBLICATIONS

ANSI/AAMI/ISO 11140-1:2005, Sterilization of health care products—Chemical indicators.
(Continued)

*Primary Examiner* — Jill Warden
*Assistant Examiner* — Julie Tavares

(57) ABSTRACT

A process challenge device comprising process challenge device comprising a container defining a space within the container, wherein the space can fully contain a process indicator; and at least one pressure-actuating valve associated with the container, wherein the at least one pressure-actuating valve regulates entrance of a sterilant into and exiting of a gas and/or liquid out of the space within the container, methods of using the device and a kit including the device are disclosed.

10 Claims, 5 Drawing Sheets

(56) References Cited

U.S. PATENT DOCUMENTS

| | | | |
|---|---|---|---|
| 4,372,916 A * | 2/1983 | Chamberlain et al. | 422/3 |
| 4,425,114 A * | 1/1984 | Schoendorfer et al. | 604/7 |
| 4,612,872 A | 9/1986 | Whelchel et al. | |
| 4,636,472 A | 1/1987 | Bruso | |
| 4,717,661 A | 1/1988 | McCormick et al. | |
| 4,752,445 A * | 6/1988 | Zell | 422/34 |
| 4,863,867 A | 9/1989 | Joyce et al. | |
| 4,914,034 A | 4/1990 | Welsh et al. | |
| 5,066,464 A | 11/1991 | Augurt | |
| 5,435,971 A | 7/1995 | Dyckman | |
| 5,565,634 A | 10/1996 | Graessle et al. | |
| 5,789,175 A | 8/1998 | Priest | |
| 5,872,004 A | 2/1999 | Bolsen | |
| 5,916,816 A | 6/1999 | Read | |
| 6,051,187 A | 4/2000 | Hughes | |
| 6,323,032 B1 | 11/2001 | Kuepper et al. | |
| 6,352,837 B1 | 3/2002 | Witcher et al. | |
| 6,623,955 B2 | 9/2003 | Matner et al. | |
| 6,630,352 B1 | 10/2003 | Reiner et al. | |
| 7,045,343 B2 | 5/2006 | Witcher et al. | |
| 7,091,042 B2 | 8/2006 | Lemus et al. | |
| 7,247,482 B2 | 7/2007 | Lemus et al. | |
| 2001/0006610 A1 | 7/2001 | Miller et al. | |
| 2002/0022246 A1 | 2/2002 | Szu-Min et al. | |
| 2003/0157588 A1 | 8/2003 | Matner et al. | |
| 2004/0256269 A1 * | 12/2004 | Gleichauf et al. | 206/439 |
| 2005/0268573 A1 | 12/2005 | Yan | |
| 2006/0234330 A1 | 10/2006 | Lemus et al. | |
| 2011/0064606 A1 | 3/2011 | Foltz et al. | |

FOREIGN PATENT DOCUMENTS

| | | |
|---|---|---|
| EP | 628814 A1 | 12/1994 |
| EP | 12012 | 5/2002 |
| EP | 1308174 | 5/2003 |
| EP | 1468701 B1 | 6/2005 |
| EP | 1550467 A1 | 7/2005 |
| GB | 1316808 A | 5/1973 |
| GB | 2186974 | 1/1987 |
| GB | 2180933 | 4/1987 |
| WO | WO 94-28164 A | 12/1994 |
| WO | WO 95-32742 A | 12/1995 |
| WO | WO 99-20790 A | 4/1999 |
| WO | WO 99-62569 A | 12/1999 |
| WO | WO 03-012459 | 2/2003 |
| WO | WO 03033034 | 4/2003 |
| WO | WO 2004-084956 A1 | 10/2004 |
| WO | WO 2005-056061 A1 | 6/2005 |
| WO | WO 2008-082728 A | 7/2008 |
| WO | WO 2009-137442 A1 | 11/2009 |
| WO | WO 2010/054095 | 5/2010 |

OTHER PUBLICATIONS

ANSI/AAMI/ISO 11138-1:2006.
Kaiser,"Which *Chemical Indicators Should be Used in a Process Challenge Device System(PCD)*" 0942-6086 Zentralsterilisation—Central Service, 15( )46—Central Service the British Library.
PCD, Features and Benifits "http://www.pcd1.com/features.html" Oct. 6, 2006.
PCD, Directions for Use, "http://www/pcd1.com/directions.html" Oct. 6, 2006.
PCD, Product Information "http://www.pcd1.com/Products.html" Oct. 6, 2006.
PCD, Ordering Information "http://www.pcd1.com/ordering.html" Oct. 6, 2006.
PCD, Validation Guide "http://www.pcd1.com/validation.html" Oct. 6, 2006.
PCD, Frequently Asked Questions "http://www.pcd1.com/faq.html" Oct. 6, 2006.

* cited by examiner

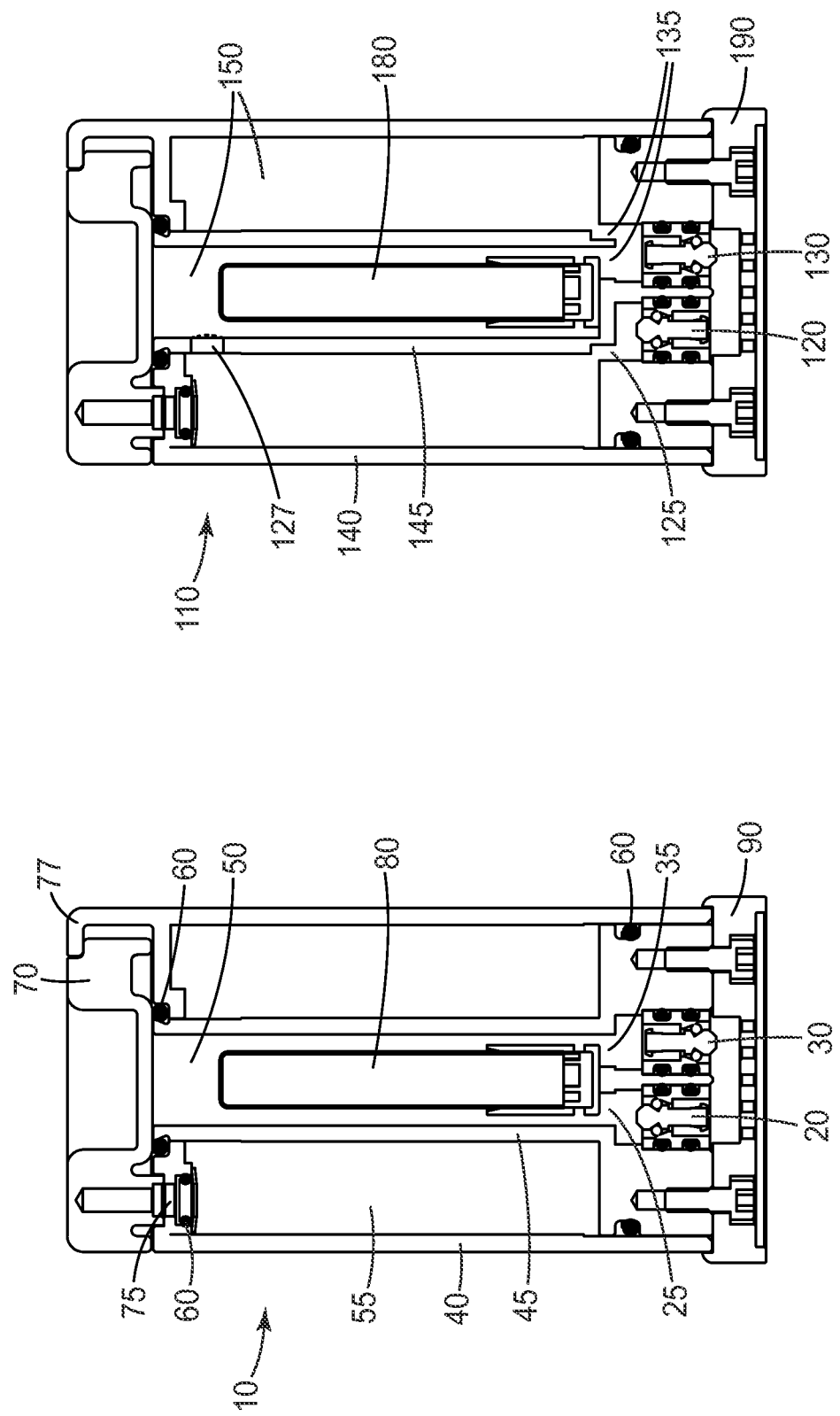

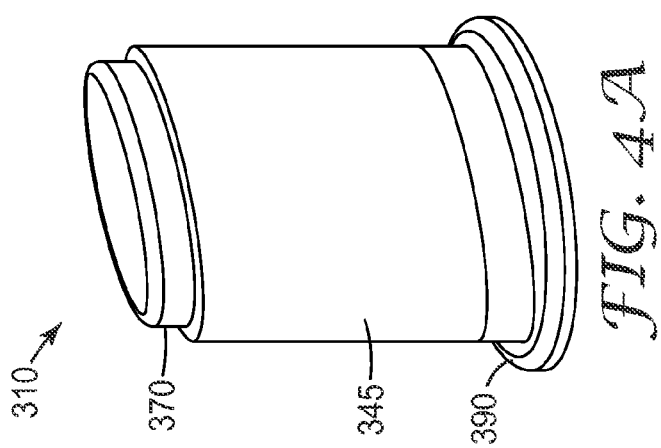
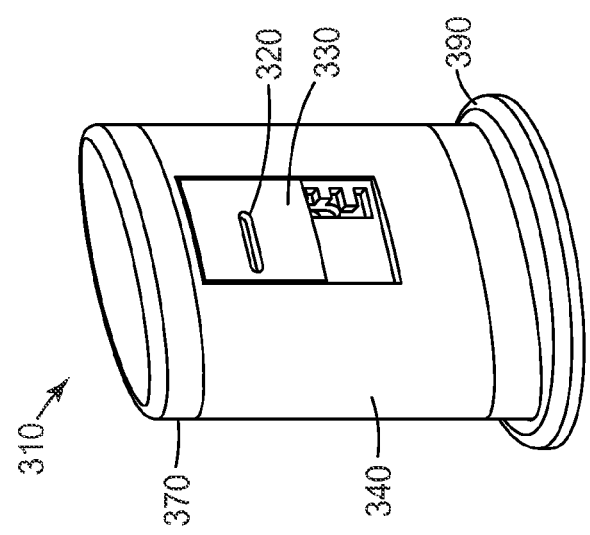
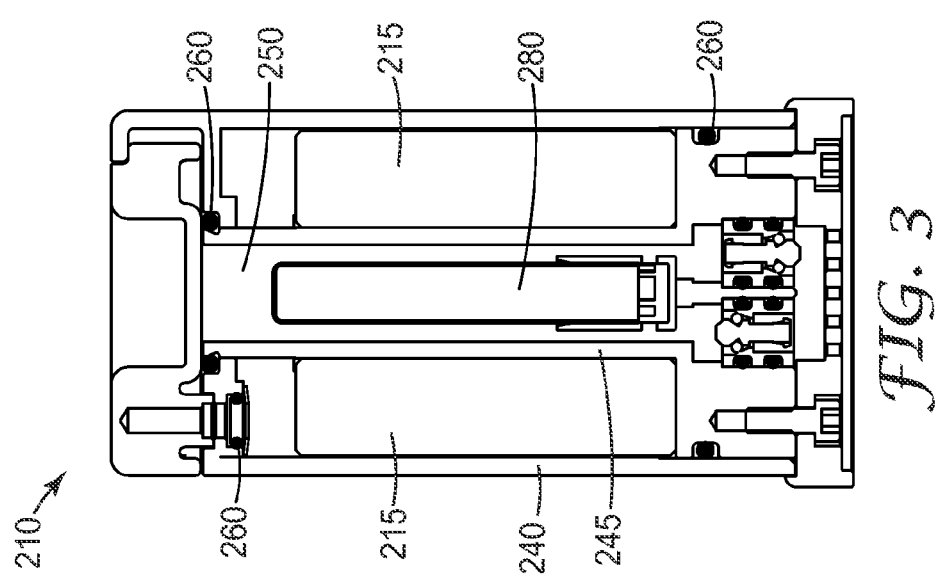

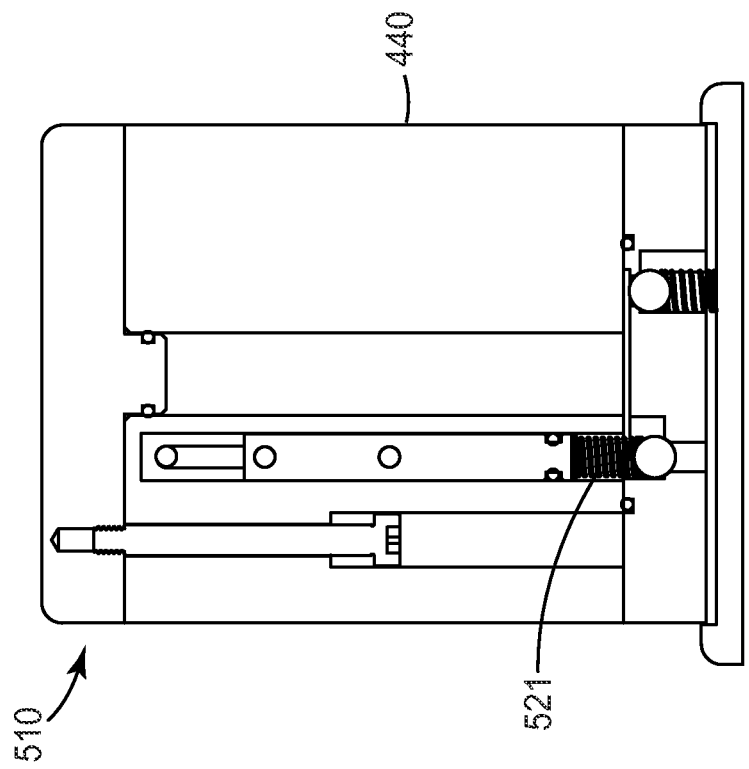
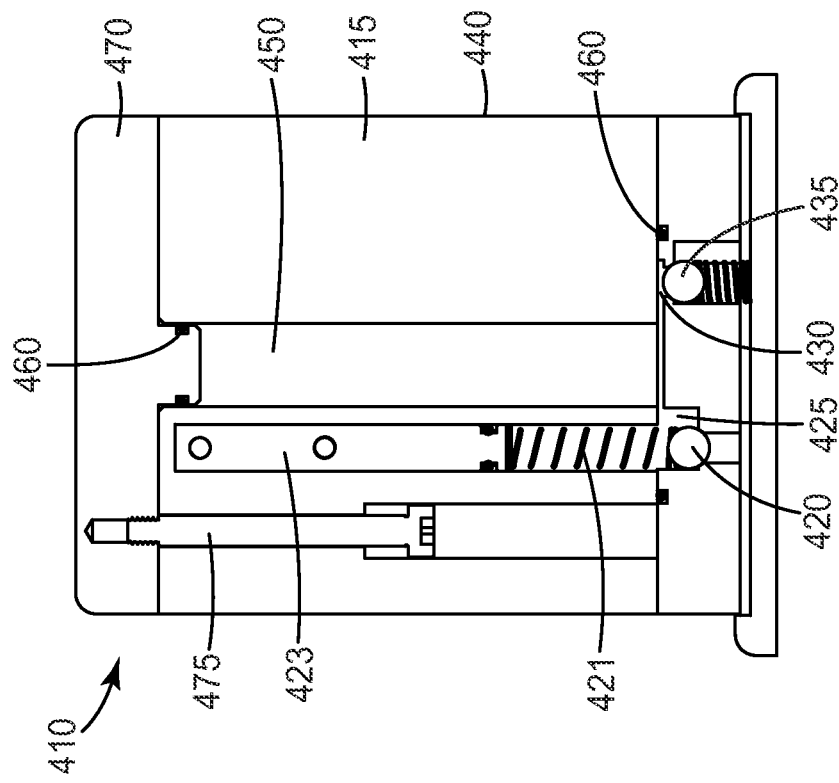
FIG. 4C
FIG. 4B

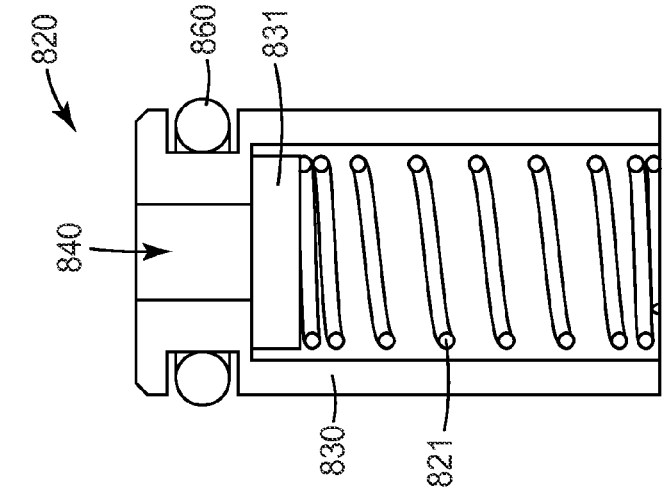
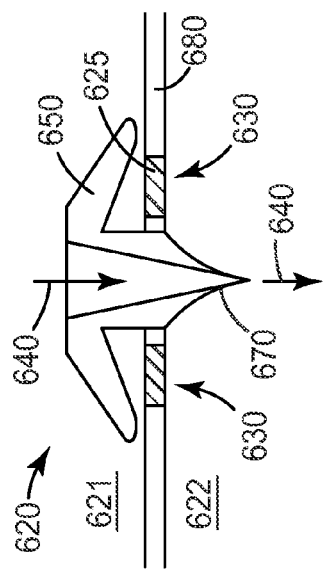
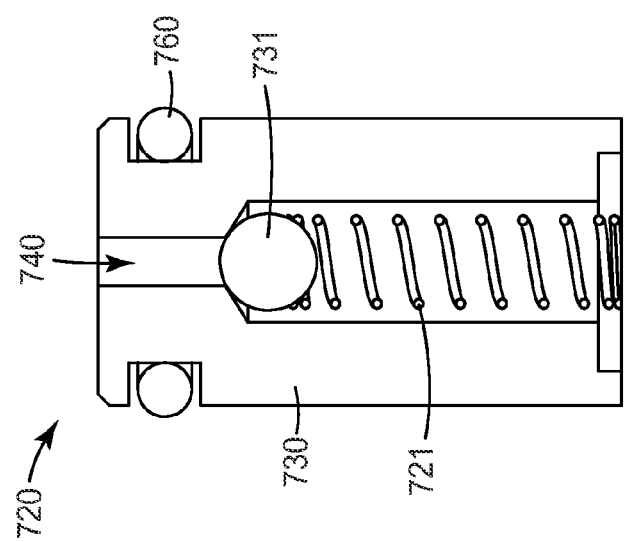

PROCESS CHALLENGE DEVICE AND METHODS

CROSS REFERENCE TO RELATED APPLICATIONS

This application is the National Stage filing under 35 U.S.C. 371 of International Application No. PCT/US2009/063330 filed Nov. 5, 2009, which claims the benefit of U.S. Provisional Application No. 61/112,071, filed Nov. 6, 2008, which is incorporated herein by reference in its entirety.

BACKGROUND

A variety of products and articles, including medical instruments, must be sterilized prior to use to prevent bio-contamination of a sample, an organism, a wound site, or the like. A number of sterilization processes are used which involve contacting the product or article with a fluid sterilant, such as a gaseous sterilant. Examples of such sterilants include, for example, steam, ethylene oxide, hydrogen peroxide, and the like.

The products and articles are generally packaged such that the sterilant can pass through the packaging, but microorganisms cannot pass through. Even though the sterilant can pass, the packaging restricts the movement of the sterilant to the product or article. Moreover, some products and articles include spaces within them that can only be reached by the sterilant via a restricted path. For example, endoscopes often include a long, narrow channel through which the sterilant must pass in order to sterilize the endoscope. These and other forms of restrictions associated with products and articles to be sterilized must be taken into account when employing a sterilization process, so that all surfaces of the product or article are exposed to the sterilant for a time sufficient to cause sterilization.

Monitoring for sufficient sterilization is generally carried out by placing an appropriate sterilization indicator along with the product and/or article to be sterilized within a sterilization chamber. A variety of sterilization indicators, including biological and chemical indicators, are known and used for this purpose. However, to take into account the above described restrictions encountered in the various products and articles, the sterilization indicator has been placed in a challenge device which restricts the flow of sterilant to the indicator using a long tortuous path. While such devices have been useful, they have not always been convenient to use and/or they have not always provided a close correlation between an indication of complete sterilization and actual complete sterilization of the product or article.

As such, there continues to be an interest in and a need for challenge devices which are convenient to use and provide a more reliable correlation between the indication of complete sterilization and actual complete sterilization of a product or article.

SUMMARY OF THE INVENTION

The present invention provides a process challenge device comprising:
a container defining a space within the container, wherein the space can fully contain a process indicator; and
at least one pressure-actuating valve associated with the container, wherein the at least one pressure-actuating valve regulates entrance of a sterilant into and exiting of a gas or liquid out of the space within the container.

The at least one pressure-actuating valve regulates the amount of gas and/or liquid that is removed from the space or the amount of vacuum that can be drawn in the space. The at least one pressure-actuating valve also regulates the amount of sterilant that can enter the space or be injected into the space under pressure. For certain embodiments, the at least one pressure-actuating valve is a combination valve. For certain embodiments, the at least one pressure-actuating valve is at least two pressure-actuating valves. For certain embodiments, a first valve regulates exiting of a gas and/or liquid out of the space, and a second valve regulates a sterilant entering the space. By selecting or adjusting the at least one valve or the at least two valves to actuate at a sufficiently high pressure or at a sufficiently low pressure, a process indicator contained within the space will require a greater or less amount of time, respectively, in a sterilization process to indicate that sterilizing conditions have been achieved.

For certain embodiments, the process challenge device further comprises a heat-transfer modulating body adjacent the indicator. For certain embodiments, the heat-transfer modulating body may be the container or a portion of the container, or the body may be a separate component which can be included with the container or added or removed from the container. For certain embodiments, at least a portion of the body at least surrounds the process indicator when present. The heat-transfer modulating body may slow the rate at which the indicator comes to the temperature of a given sterilization process. For certain embodiments, the heat-transfer modulating body may also increase the time required for the sterilant to contact the indicator sufficiently to bring about an indication that sterilization conditions have been achieved.

For certain embodiments, the space further contains a volume of gas, for example, air, nitrogen, carbon dioxide, or another inert gas. The volume of gas contained within the space has been found to provide a resistance to the sterilant which can be controlled and used effectively to provide a challenge device which can correlate well with sterilization of a variety of products and articles and quantities thereof. Displacement of the gas is carried out in order for the sterilant to fill the space and sufficiently contact the indicator.

For certain embodiments, the device further comprises a port in fluid communication with the space within the container, wherein a condensate can exit out of the space through the port. For certain embodiments, as an alternative to the port or in addition to the port, the device further comprises an absorbent material within the space and adjacent the process indicator when present. Whether a port, an absorbent material, a combination of these, or other means are used to reduce or eliminate the amount of condensate that may contact the process indicator when present, in certain embodiments, doing so may increase the reproducibility of an indication by the process indicator that sterilizing conditions have or have not been achieved.

In another embodiment, there is provided method of determining the effectiveness of a sterilization process, the method comprising:
providing a process challenge device of any one of the embodiments described herein; wherein the space within the container fully contains a process indicator;
positioning the process challenge device in a sterilization chamber;
exposing the process challenge device to a sterilant at an elevated temperature; and
determining whether or not the process indicator indicates that it has been exposed to sterilization process conditions effective for sterilizing an article.

In another embodiment, there is provided a kit comprising at least one process challenge device of any one of the embodiments thereof described herein; and a plurality of sterilization process indicators for the same or different sterilization processes.

In another embodiment, there is provided a method of controlling the level of resistance to a sterilization process provided by a process challenge device, the method comprising:

providing a process challenge device comprising:
a container defining a space within the container, wherein the space can fully contain a process indicator; and
at least one pressure-actuating valve associated with the container, wherein the at least one pressure-actuating valve regulates entrance of a sterilant into and exiting of a gas and/or liquid out of the space within the container;

wherein the process challenge device further comprises a feature for controlling the level of resistance, the feature selected from the group consisting of:

at least one pressure-actuated valve can be adjusted to increase or decrease the pressure difference required to actuate the valve;
the space further contains a volume of gas, wherein the volume can be adjusted to a volume of at least 5 cubic centimeters and not more than 1000 cubic centimeters.
the device further comprises a heat-transfer modulating body, wherein at least a portion of the body at least surrounds the process indicator when present, the at least a portion of the heat-transfer modulating body comprises walls which at least surround the indicator when present; and
a combination thereof;

adjusting the sterilization process challenge device to provide a targeted level of resistance to a sterilization process; wherein adjusting comprises a step selected from the group consisting of:

adjusting the at least one pressure-actuated valve;
adjusting the volume of the gas,
adjusting the thickness of the heat-transfer modulating body walls;
adjusting a thermal diffusivity of the heat-transfer modulating body; and
a combination thereof.

The above summary of the present invention is not intended to describe each disclosed embodiment or every implementation of the present invention. The description that follows more particularly exemplifies illustrative embodiments.

DEFINITIONS

The term "heat-transfer modulating body" refers to a body which controls the time required to raise the temperature of an indicator adjacent the body to the sterilization process temperature. For example, where a steam sterilization process temperature is 132° C., the heat-transfer modulating body increases the time required for the indicator to reach 132° C. by slowing the rate at which heat is transferred to the indicator from, for example, a sterilization chamber.

The term "surround" refers to a heat-transfer modulating body or walls of the body positioned at least partially around the indicator but not completely enclosing the indicator.

The terms "envelop" or "enveloping" refer to a heat-transfer modulating body or walls of the body positioned to completely enclose the indicator.

The term "impervious to the sterilant" refers to walls that do not allow sterilant to pass through, except where an opening is provided to allow sterilant to enter any space defined by the walls. For example, the walls may be comprised of a continuous material which is not porous to the sterilant.

The term "pervious to the sterilant" refers to a heat-transfer modulating body or a wall or walls of the body that allow sterilant to pass through the body or the walls. For example, the body or walls may be comprised of a material which is porous to the sterilant, and/or the body or walls may include a plurality of openings or spaces through which the sterilant may pass.

The term "comprising" and variations thereof (e.g., comprises, includes, etc.) do not have a limiting meaning where these terms appear in the description and claims.

As used herein, "a," "an," "the," "at least one," and "one or more" are used interchangeably, unless the context clearly dictates otherwise.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

Also herein, the recitations of numerical ranges by endpoints include all numbers subsumed within that range (e.g., a volume of 5 to 1000 $cm^3$ includes a volume of 5, 63, 75.5, 1000 $cm^3$ etc.).

BRIEF DESCRIPTIONS OF THE DRAWINGS

FIG. 1 is a schematic cross-section view of one embodiment of a device according to the present invention.

FIG. 2 is a schematic cross-section view of another embodiment of a device according to the present invention.

FIG. 3 is a schematic cross-section view of another embodiment of a device according to the present invention, wherein the device includes one embodiment of a heat-transfer modulating body.

FIG. 4 is a perspective view of another embodiment of a device according to the present invention.

FIG. 4A is a perspective view of another embodiment of a device according to the present invention, wherein the device includes another embodiment of a heat-transfer modulating body.

FIG. 4B is a schematic cross-section view of another embodiment of a device according to the present invention, wherein the device includes one embodiment of a pressure-actuating valve adjusted to actuate at a relatively low pressure.

FIG. 4C is a schematic cross-section view of another embodiment of a device according to the present invention, wherein the device includes one embodiment of a pressure-actuating valve adjusted to actuate at a relatively high pressure.

FIG. 5 is a schematic cross-section view of a combination valve which can be used in certain embodiments of a device according to the present invention.

FIG. 6 is a schematic cross-section view of one alternative valve which can be used in certain embodiments of a device according to the present invention.

FIG. 7 is a schematic cross-section view of another alternative valve which can be used in certain embodiments of a device according to the present invention.

DETAILED DESCRIPTION OF ILLUSTRATIVE EMBODIMENTS OF THE INVENTION

Figure 8:
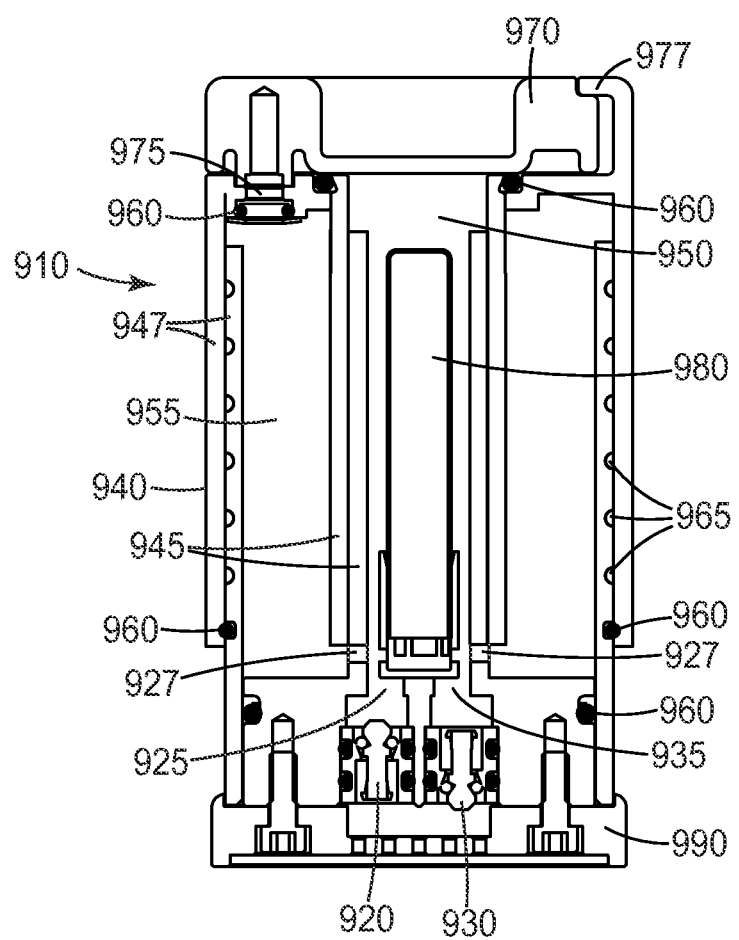
FIG. 8 is a schematic cross-section view of another embodiment of a device according to the present invention, wherein the device can be adjusted for different volumes of space within the container of the device.

Process challenge device 10 illustrated in FIG. 1 is one embodiment of a process challenge device described herein. Container 40 includes walls 45 which define space 50 within container 40. The space 50 can contain process indicator 80 which is illustrated as being present in FIG. 1, although the presence of indicator 80 is not required in all embodiments described herein. Process indicator 80 or any process indicator referred to in any of the embodiments described herein can be one or more indicators and one or more types of indicators, for example, a biological indicator (BI) and/or a chemical indicator (CI). Optional outer space 55 can act as a heat-transfer modulating body by slowing the rate at which space 50 and indicator 80 when present come to a sterilization process temperature. Pressure-actuating valves 20 and 30 associated with container 40 are illustrated as poppet style check valves. However, various other valve designs, for example, as those illustrated in FIGS. 4A and 4B, 5, 6, and 7 may be used. Valve 20 is actuated when the pressure outside of the container 40 is higher than the pressure in space 50. Valve 30 is actuated when the pressure in space 50 is higher than outside the container 40. Valves 20 and 30 can be chosen to actuate at a particular pressure, for example at a pressure of 68.95 Pa (10 psi). Valves 20 and 30 can be chosen to actuate at the same pressure or at a different pressure. Pressure-actuating valve 20 regulates entrance of a sterilant into space 50 through port 25. Pressure-actuating valve 30 regulates exiting of a gas and/or a liquid out of space 50 through port 35. Seals 60 reduce or eliminate leakage of any gas and/or liquid into or out of space 50 and outer space 55. This provides one embodiment whereby the container can be sealed or the container is sealed, such that essentially all of any sterilant flow into and essentially all of any gas and/or liquid flow out of the space within the container passes through at least one pressure-actuating valve.

The device 10 also includes a lid 70, which can pivot about pivot 75 to allow positioning indicator 80 within space 50 and removing indicator 80 from space 50. Housing 77 of container 40 holds lid 70 in a closed position by friction or other locking means.

Base 90 holds valves 20 and 30 in place, although other known fasteners and locking mechanisms can be used to hold valves 20 and 30 in place. Base 90 also provides a convenient base for positioning device 10 in a sterilization chamber or on any surface so as to remain stable in the upright position shown in FIG. 1.

Process challenge device 110 illustrated in FIG. 2 is another embodiment of a process challenge device described herein. Device 110 differs from device 10 in FIG. 1 in that it includes port 127 and different port configurations for sterilant entry and gas/liquid exit. In device 110, space 150 is extended, using port 127, to include space 55 illustrated in FIG. 1, thereby increasing the volume of space 150 and providing an increased challenge to a sterilization process. Container 140 includes walls 145 which define the space where a process indicator as described in FIG. 1 can be positioned as illustrated by process indicator 180. A sterilant entering space 150 is regulated by valve 120 associated with container 140 and passes through port 125. The entering sterilant enters the space where indicator 180 is positioned through port 127. A gas and/or a liquid exiting space 150 is regulated by valve 130 associated with container 140 and passes through port 135, which is illustrated as being in fluid communication with the outer space included with space 150 and also as being in fluid communication with the space defined by walls 145 wherein indicator 180 is positioned. The device thereby has at least a portion of gas and/or liquid exiting and sterilant entering the space defined by walls 145 at opposite ends of the space defined by walls 145. In one alternative, port 135 can be limited to fluid communication with the space defined by walls 145 wherein indicator 180 is positioned. For certain embodiments, any condensate forming in the space defined by walls 145 wherein indicator 180 is positioned can exit the space through port 135. The valves 120 and 130 can be any of the valves described for valves 20 and 30 in FIG. 1. The valves 120 and 130 can be held in place with base 190 as illustrated in FIG. 2 or by other known fasteners and locking mechanisms.

Process challenge device 210 illustrated in FIG. 3 is another embodiment of a process challenge device described herein. Device 210 is similar to device 10 illustrated in FIG. 1, but includes a solid heat-transfer modulating body 215 positioned between walls 245 and outer walls of container 240. The body 215 is illustrated as surrounding the process indicator 280 positioned within space 250 defined by walls 245. For certain embodiment, alternatively, body 215 can only partially surround indicator 280. Seals 260 reduce or eliminate leakage of any gas and/or liquid into or out of space 250 and the space wherein body 215 resides.

Process challenge device 310 illustrated in FIG. 4 is another embodiment of a process challenge device described herein and includes an adjustable pressure-actuating valve which can be adjusted using adjustment lever 330. The adjustment can be made for using the device in a selected sterilization process. Device 310 further includes optional code window 320, which can reveal a code designating the selected sterilization process. The code can be a name, number, bar code, or other designating code. Device 310 includes container 340 defining a space therein which can be accessed for positioning or removing a process indicator by opening lid 370. Base 390 holds device 310 in the upright position shown in FIG. 4.

Process challenge device 310 illustrated in FIG. 4A is the same as the device of FIG. 4, but includes heat-transfer modulating body 345 outside of container 340 illustrated in FIG. 4. Body 345 may extend to base 390 or part way to base 390. Lid 370 can be opened with body 345 positioned as shown in FIG. 4A. However, in certain embodiments, body 345 extends over edges of lid 370, such that body 345 holds lid 370 in the closed position and is removed or moved toward base 390 to open lid 370.

Process challenge device 410 illustrated in FIG. 4B is another embodiment of a process challenge device described herein and is similar to the devices illustrated in FIGS. 4 and 4A. Adjustable pressure-actuating valve 420 is a ball valve with spring 421 and spring plunger 423. Spring plunger can be positioned to increase or decrease the tension of spring 421. The positioning can be carried out and then held in place by a lever, such as lever 330 illustrated in FIG. 4. FIG. 4B illustrates spring 421 under low tension such that valve 420 can be actuated at a relatively low pressure. A sterilant under pressure greater than the pressure in space 450 and sufficient to overcome the tension exerted by spring 421 can enter space 450 by passing through port 425. Valve 420 thereby regulates the sterilant entering space 450. Pressure-actuating valve 435 regulates exiting of a gas and/or a liquid out of space 450 through port 430. When the pressure difference between space 450 and outside container 440 is sufficient to overcome the tension holding valve 435 in the closed position, valve 435 actuates and allows the gas and/or the liquid out of space 450 through port 430, the pressure in space 450 being higher than outside container 440. Various seals are included in device 410, such as seals 460, to prevent a sterilant or a gas and/or a liquid from entering space 450 other than through valves 420 and 435, respectively. Pivot 475 allows lid 470 to be lifted away from container 440 and pivoted about pivot 475 for access to space 450, so that a process indicator can be place within space 450 and later removed. The walls 415 of container 440 define space 450 and can further act as a heat-transfer modulating body, which increases the time required for the temperature of space 450 and a process indicator if present to reach the temperature of a sterilization process.

Process challenge device 510 illustrated in FIG. 4C illustrates spring 421 shown in FIG. 4B under its highest tension. The device 510 thereby illustrates the devices illustrated in FIGS. 4, 4A, and 4B adjusted to an increased level of resistance to a sterilization process, since sterilant can only access space 450 illustrated in FIG. 4B when at a relatively high pressure.

As indicated above, various valve designs may be used in the device described herein. Combination valve 620 illustrated in FIG. 5 regulates both flow 630 and 640. Such a valve can be used to regulate both entrance of a sterilant and exiting of a gas and/or liquid. Combination valve 620 allows flow 630 through ports 625 when the pressure on side 622 is sufficient to lift umbrella 650 off of housing 680 as shown in FIG. 5. For example, when side 622 is outside of the container of a process challenge device and side 621 is in fluid communication with the space within the container, a sterilant may pass from side 622 to 621 through ports 625 when the pressure outside the container is greater than the pressure in the space. Combination valve 620 allows flow 640 when the pressure on side 621 is higher than on side 622, forcing umbrella 650 against housing 680 and opening duck bill 670. In the above example, a gas and/or liquid can then exit through duck bill 670.

Ball valve 720 illustrated in FIG. 6 regulates flow 740, such that when sufficient pressure is exerted against ball 731 to overcome the tension of spring 721 against ball 731 and any gas pressure on the spring 721 side of ball 731 flow 740 occurs. Seal 760 prevents leakage around valve 720 when seated in a housing (not shown). Two or more ball valves 720 may be used by positioning the valves to allow flow both into and out of the space within a container of a process challenge device.

Valve 820 illustrated in FIG. 7 regulates flow 840, such that when sufficient pressure is exerted against valve pad 831 to overcome the tension of spring 821 against valve pad 831 and any gas pressure on the spring 821 side of valve pad 831 flow 840 occurs. Seal 860 prevents leakage around valve 820 when seated in a housing (not shown). Two or more valves 820 may be used by positioning the valves to allow flow both into and out of the space within a container of a process challenge device.

Process challenge device 910 illustrated in FIG. 8 is another embodiment of a process challenge device described herein. Process challenge device is similar to device 10 illustrated in FIG. 1, but the volume within space 950 can be increased by sliding the end of container 940 which includes lid 970 away from the end of container 940 which includes the base 990. A series of grooves 965 positioned in one of the outer container walls 947, to which a seal 960 mates, can provide specific predetermined volume settings. Container 940 includes walls 945 which define space 950 within container 940. The space 950 is further extended to include outer space 955 via ports 927. The space 950 can contain process indicator 980 which is illustrated as being present in FIG. 8, although the presence of indicator 980 is not required in all embodiments described herein. Process indicator 980 or any process indicator referred to in any of the embodiments described herein can be one or more indicators and one or more types of indicators, for example, a biological indicator (BI) and/or a chemical indicator (CI). Outer space 955 can act as a heat-transfer modulating body by slowing the rate at which space 950 and indicator 980 when present come to a sterilization process temperature. Although not shown, outer space 955 may further contain a solid heat-transfer modulating body. Pressure-actuating valves 920 and 930 associated with container 940 are illustrated as poppet style check valves. However, various other valve designs, for example, as those illustrated in FIGS. 4A and 4B, 5, 6, and 7 may be used. Valve 920 is actuated when the pressure outside of the container 940 is higher than the pressure in space 950. Valve 930 is actuated when the pressure in space 950 is higher than outside the container 940. Valves 920 and 930 can be chosen to actuate at a particular pressure, for example at a pressure of 68.95 Pa (10 psi). Valves 920 and 930 can be chosen to actuate at the same pressure or at a different pressure. Pressure-actuating valve 920 regulates entrance of a sterilant into space 950 through port 925. Pressure-actuating valve 930 regulates exiting of a gas and/or a liquid out of space 950 through port 935. Seals 960 reduce or eliminate leakage of any gas and/or liquid into or out of space 950 and outer space 955.

The device 910 also includes a lid 970, which can pivot about pivot 975 to allow positioning indicator 980 within space 950 and removing indicator 980 from space 950. Housing 977 of container 940 holds lid 970 in a closed position by friction or other locking means.

For certain embodiments, the walls comprising any one of the embodiments of a heat-transfer modulating body described herein have a thickness of at least 0.3 cm. The walls may include one, two, three, or more layers. The heat-transfer modulating body can be adjusted for wall thickness by removing one or more layers, and thereby decrease the resistance of the device to sterilization conditions. Also, one or more additional layers can be added to increase the wall thickness of the heat-transfer modulating body, and thereby increase the resistance of the device to sterilization conditions. Moreover, the layers can have the same or different thermal diffusivities, allowing the thermal diffusivity of the heat-transfer modulating body to be adjusted for a particular sterilization process. For certain embodiments, preferably the walls of the heat-transfer modulating body have a thermal diffusivity (a) of not more than $1 \times 10^{-5}$ m$^2$/s at 20° C.

The process challenge devices described herein can be provided without or with one or more process indicators. The indicator or indicators are chosen to be used with sterilization conditions to be employed in a particular sterilization process. When the device is provided without the indicator, the indicator is selected and placed in the device prior to using the device in the sterilization process. For example, for a steam sterilization process, a steam sterilization indicator is selected for indicator. Moreover, the indicator can be chosen based upon the amount of exposure to sterilization conditions required to cause the indicator to indicate that the exposure has occurred. The choice of the sterilization indicator can thereby by used to increase or decrease the resistance of the sterilization process challenge device.

When absorbent material is present, the space within the container is dimensioned to allow the indicator and absorbent material to fit within the space. The absorbent material can absorb the condensate of a sterilant to prevent or reduce the amount of condensate that can contact the sterilization indicator, thereby preventing undesired indicator error. Furthermore, preventing condensate formation on the indicator reduces the heat gain of the indicator caused by heat transfer from the sterilant. For example, with steam sterilization, the absorbent material absorbs water which would otherwise condense on the indicator. A suitable absorbent material is cellulose or other absorbent fiber, such as absorbent paper.

The absorbent material can extend beyond the ends of the indicator, such that when placed within a space within a container, the indicator can be retrieved from the space by pulling on the absorbent material.

For certain embodiments, when an indicator is within a space within a container, the distance between indicator and the walls defining the space is preferably less than 5 cm. For certain embodiments the distance is less than 2 cm, 1 cm, 0.75 cm, or 0.5 cm. For certain embodiments, the indicator can contact the walls. Preferably, the distance between the indicator and the walls is sufficient to allow a layer of absorbent material between the walls and the indicator.

The process challenge device of the present invention can be provided without or with an indicator, which is chosen to be used with sterilization conditions to be employed in a particular sterilization process. As indicted above, the indicator can be a BI, a CI, a combination thereof. A plurality of indicators can also be used in the process challenge device. When the device is provided without an indicator, an indicator is selected and placed in the device prior to using the device in a sterilization process. The indicator or indicators can be covered with a porous material, such as paper or fabric. For certain embodiments, the indicator is sandwiched between or wrapped in two or more layers of a porous material. For certain embodiments, preferably the porous material absorbs sterilant condensate.

As indicated above, for certain embodiments, the space within the container further contains a volume of gas of at least 5 cm$^3$. For certain embodiments, including any one of the above embodiments of the device described herein, the volume of gas contained within the space is at least 10, 25, or 50 cm$^3$. For certain of these embodiments, the volume of gas contained within the space is not more 1000 cm$^3$, 500 cm$^3$, 250 cm$^3$, 125 cm$^3$, or 75 cm$^3$.

As indicated above, for certain embodiments, the walls comprising any one of the heat-transfer modulating bodies described herein have a thickness of at least 0.3 cm. For certain embodiments, including any one of the embodiments of the device described herein, the thickness is preferably at least about 0.5 cm. For certain of these embodiments, the thickness is at least 0.6 cm, 0.75 cm, 1 cm, 1.25 cm, or 2.5 cm. For certain embodiments, the thickness is at most 10 cm or 5 cm.

For certain embodiments, the walls comprising any one of the heat-transfer modulating bodies described herein have a thermal diffusivity (a) of not more than $1 \times 10^{-5}$ m$^2$/s at 20° C. Suitable materials for the walls of the body include, for example, stainless steel ($\alpha = 0.405 \times 10^{-5}$ m$^2$/s), polypropylene, DELRIN, nylon ($\alpha = 1.3 \times 10^{-7}$ m$^2$/s), polyester, polycarbonate, polytetrafluoroethylene ($\alpha = 1.1 \times 10^{-7}$ m$^2$/s), and the like. For certain of these embodiments, the thermal diffusivity is not more than $5 \times 10^{-7}$ m$^2$/s at 20° C. For certain of these embodiments, the thermal diffusivity is not more than $2 \times 10^{-7}$ m$^2$/s at 20° C. The thermal diffusivity of the material indicates how rapidly the material adjusts its temperature to that of its surroundings. For example, a material with a relatively low thermal diffusivity heats up more slowly than a material with a higher thermal diffusivity in an environment at an elevated temperature, such as a sterilization chamber. Thermal diffusivity is used in heat transfer analysis and is the ratio of thermal conductivity to volumetric heat capacity as follows:

$$\alpha = \kappa / \rho C_p$$

where $\kappa$ is thermal conductivity (W/mK), $\rho$ is density (kg/m$^3$), and $C_p$ is specific heat capacity (J/kgK). Thus, using these parameters, a suitable material or combination of materials for the walls of the heat-transfer modulating body can be chosen to achieve a desired resistance to sterilization conditions used in a sterilization process. For example, a material with a particular thermal diffusivity can be used for the walls of the heat-transfer modulating body, or the walls of the heat-transfer modulating body can be comprised of two or more layers, where at least two of the layers have different thermal diffusivities, to provide walls with a composite thermal diffusivity.

Sterilization indicators which can be used in the process challenge device described herein are known and include biological indicators and chemical indicators. Examples of biological indicators include ATTEST 1292 Rapid Biological Indicators (available from 3M Company, St. Paul, Minn.) and those described in U.S. Pat. No. 6,623,955 can be used. Examples of chemical indicators include COMPLY STERI-GAGE 1243 Steam Chemical Integrator (available from 3M Company) and those described in U.S. Pat. No. 5,916,816 can be used.

The following is a list of certain exemplary embodiments of the present invention.

1. A process challenge device comprising:
   a container defining a space within the container, wherein the space can fully contain a process indicator; and
   at least one pressure-actuating valve associated with the container, wherein the at least one pressure-actuating valve regulates entrance of a sterilant into and exiting of a gas or liquid out of the space within the container.
2. The device of embodiment 1, wherein the at least one pressure-actuating valve is a combination valve.
3. The device of embodiment 1 or embodiment 2, wherein the at least one pressure-actuating valve is actuated when there is a pressure difference between the space within the container and outside of the first container.
4. The device of embodiment 1 or embodiment 2, wherein the at least one pressure-actuating valve is at least two pressure-actuating valves.
5. The device of embodiment 4, wherein the at least two pressure-actuating valves are each independently actuated when there is a pressure difference between the space within the container and outside of the first container.
6. The device of embodiment 4, wherein a first pressure-actuating valve regulates entrance of a sterilant into the space within the container, and a second pressure-actuating valve regulates exiting of a gas and/or a liquid out of the space within the container.
7. The device of embodiment 6, wherein the first pressure-actuating valve and the second pressure-actuating valve are each independently actuated when there is a pressure difference between the space within the container and outside of the container.
8. The device of any one of embodiments 3, 5, and 7, wherein the pressure difference at which at least one pressure-actuating valve is actuated can be adjusted.
9. The device of any one of embodiments 3, 5, 7, and 8, wherein the pressure difference is at least 6.895 kPa (1 psi).
10. The device of any one of embodiments 3, 5, 7, 8, and 9, wherein the pressure difference is not more than 345 kPa (50 psi).

11. The device of embodiment 10, wherein the pressure difference is not more than 172.4 kPa (25 psi).
12. The device of any one of embodiments 1 through 11, wherein the container can be sealed or the container is sealed, such that essentially all of any sterilant flow into and essentially all of any gas and/or liquid flow out of the space within the container passes through at least one pressure-actuating valve.
13. The device of any one of embodiments 1 through 12, further comprising a port in fluid communication with the space within the container, wherein a condensate can exit out of the space through the port.
14. The device of embodiment 13 as dependent on embodiments 6, 7, and 8 through 12 as dependent on embodiment 6 or embodiment 7, wherein the second pressure-actuating valve regulates exiting of the condensate out of the space within the container.
15. The device of any one of embodiments 1 though 14, further comprising an absorbent material within the space and adjacent the process indicator when present.
16. The device of any one of embodiments 1 through 15, wherein the space further contains a volume of gas of at least 5 cubic centimeters.
17. The device of embodiment 16, wherein the volume of gas is not more than 1000 cubic centimeters.
18. The device of any one of embodiments 1 through 17, wherein the device further comprises a heat-transfer modulating body, wherein at least a portion of the body at least surrounds the process indicator when present.
19. The device of embodiment 18, wherein the at least a portion of the heat-transfer modulating body comprises walls which surround the indicator when present.
20. The device of embodiment 19, wherein the heat-transfer modulating body walls have a thickness of at least 0.3 cm.
21. The device of embodiment 20, wherein the thickness is adjustable by adding or removing at least one wall layer, wherein the at least one wall layer nests with another wall layer after being added or prior to being removed, to provide the thickness of the walls.
22. The device of any one of embodiments 19, 20, and 21, wherein the walls are impervious to the sterilant.
23. The device of embodiment 18, wherein the at least a portion of the heat-transfer modulating body envelops the indicator when present; and wherein at least a portion of the body enveloping the indicator is pervious to the sterilant.
24. The device of embodiment 23, wherein the at least a portion of the heat-transfer modulating body comprises walls which envelop the indicator when present.
25. The device of embodiment 24, wherein the heat-transfer modulating body walls have a thickness of at least 0.3 cm.
26. The device of embodiment 25, wherein the thickness is adjustable by adding or removing at least one wall layer, wherein the at least one wall layer nests with another wall layer after being added or prior to being removed, to provide the thickness of the walls.
27. The device of any one of embodiments 24, 25, and 26, wherein at least a portion of the walls is pervious to the sterilant.
28. The device of any one of embodiments 1 through 27, wherein the space fully contains a process indicator.
29. A method of determining the effectiveness of a sterilization process, the method comprising:
providing a process challenge device of any one of embodiments 1 through 27; wherein the space within the container fully contains a process indicator;
positioning the process challenge device in a sterilization chamber;
exposing the process challenge device to a sterilant at an elevated temperature; and
determining whether or not the process indicator indicates that it has been exposed to sterilization process conditions effective for sterilizing an article.
30. The method of embodiment 29, further comprising positioning the process indicator in the space within the container such that the space fully contains the process indicator.
31. The method of embodiment 29 or embodiment 30, further comprising positioning the article in the sterilization chamber.
32. A kit comprising at least one process challenge device of any one of embodiments 1 through 28; and a plurality of sterilization process indicators for the same or different sterilization processes.
33. The kit of embodiment 32, further comprising a plurality of heat-transfer modulating bodies, each having the same or different thermal diffusivities and the same or different wall thicknesses.
34. The kit of embodiment 32 or embodiment 33, wherein the kit comprises a plurality of process challenge devices, and wherein the spaces within the containers have the same volumes or different volumes.
35. A method of controlling the level of resistance to a sterilization process provided by a process challenge device, the method comprising:
providing a process challenge device comprising:
a container defining a space within the container, wherein the space can fully contain a process indicator; and
at least one pressure-actuating valve associated with the container, wherein the at least one pressure-actuating valve regulates entrance of a sterilant into and exiting of a gas and/or liquid out of the space within the container;
wherein the process challenge device further comprises a feature for controlling the level of resistance, the feature selected from the group consisting of:
at least one pressure-actuated valve can be adjusted to increase or decrease the pressure difference required to actuate the valve;
the space further contains a volume of gas, wherein the volume can be adjusted to a volume of at least 5 cubic centimeters and not more than 1000 cubic centimeters.
the device further comprises a heat-transfer modulating body, wherein at least a portion of the body at least surrounds the process indicator when present, the at least a portion of the heat-transfer modulating body comprises walls which at least surround the indicator when present; and
a combination thereof;
adjusting the sterilization process challenge device to provide a targeted level of resistance to a sterilization process;
wherein adjusting comprises a step selected from the group consisting of:
adjusting the at least one pressure-actuated valve;
adjusting the volume of the gas,
adjusting the thickness of the heat-transfer modulating body walls;
adjusting a thermal diffusivity of the heat-transfer modulating body; and
a combination thereof.
36. The method of embodiment 35, wherein at least one pressure-actuating valve is a combination valve.
37. The method of embodiment 35 or embodiment 36, wherein the at least one pressure-actuating valve is actuated when there is a pressure difference between the space within the container and outside of the first container.

38. The method of any one of embodiments 35, 36, and 37, wherein the at least one pressure-actuating valve is at least two pressure-actuating valves.
39. The method of embodiment 38, wherein the at least two pressure-actuating valves are each independently actuated when there is a pressure difference between the space within the container and outside of the first container.
40. The method of embodiment 39, wherein a first pressure-actuating valve regulates entrance of a sterilant into the space within the container, and a second pressure-actuating valve regulates exiting of a gas and/or a liquid out of the space within the container.
41. The method of embodiment 40, wherein the first pressure-actuating valve and the second pressure-actuating valve are each independently actuated when there is a pressure difference between the space within the container and outside of the container.
42. The method of any one of embodiments 35 through 41, wherein at least one pressure-actuated valve can be adjusted to increase or decrease the pressure difference required to actuate the valve.
43. The method of any one of embodiments 37, 39, 41, and 42, wherein the pressure difference is at least 6.895 kPa (1 psi).
44. The method of any one of embodiments 37, 39, 41, 42, and 43, wherein the pressure difference is not more than 345 kPa (50 psi).
45. The method of embodiment 44, wherein the pressure difference is not more than 172.4 kPa (25 psi).
46. The method of any one of embodiments 35 through 45, wherein the container can be sealed or the container is sealed, such that essentially all of any sterilant flow into and essentially all of any gas and/or liquid flow out of the space within the container passes through at least one pressure-actuating valve.
47. The method of any one of embodiments 35 through 46, further comprising a port in fluid communication with the space within the container, wherein a condensate can exit out of the space through the port.
48. The method of embodiment 47 as dependent on embodiments 40, 41, and 42 through 47 as dependent on embodiment 40 or embodiment 41, wherein the second pressure-actuating valve regulates exiting of the condensate out of the space within the container.
49. The method of any one of embodiments 35 through 48, wherein the space further contains a volume of gas of at least 5 cubic centimeters.
50. The method of embodiment 49, wherein the volume of gas is not more than 1000 cubic centimeters.
51. The method of embodiment 49, where the volume can be adjusted to a volume of at least 5 cubic centimeters and not more than 1000 cubic centimeters.
52. The method of any one of embodiments 35 through 51, wherein the device further comprises a heat-transfer modulating body, wherein at least a portion of the body at least surrounds the process indicator when present.
53. The method of embodiment 52, wherein the at least a portion of the heat-transfer modulating body comprises walls which surround the indicator when present, the walls having a thickness.
54. The method of embodiment 53, wherein the heat-transfer modulating body walls have a thickness of at least 0.3 cm.
55. The method of embodiment 53 or embodiment 54, wherein the heat-transfer modulating body walls are comprised of at least one layer.
56. The method of embodiment 55, wherein the thickness is adjustable by adding or removing at least one wall layer, to provide the thickness of the walls.
57. The method of embodiment 55 or embodiment 56, wherein the thermal diffusivity of the heat-transfer modulating body can be adjusted by exchanging at least one wall layer for another having a lower or higher thermal diffusivity.
58. The method of any one of embodiments 52 through 57, wherein the thermal diffusivity of the heat-transfer modulating body can be adjusted by exchanging the body for another body having a lower or higher thermal diffusivity.
59. The method of any one of embodiments 53 through 58, wherein the walls of the heat-transfer modulating body are impervious to the sterilant.
60. The method of embodiment 52, wherein the at least a portion of the heat-transfer modulating body envelops the indicator when present; and wherein at least a portion of the body enveloping the indicator is pervious to the sterilant.
61. The method of embodiment 60, wherein the at least a portion of the heat-transfer modulating body comprises walls which envelop the indicator when present, the walls having a thickness.
62. The method of embodiment 61, wherein the heat-transfer modulating body walls have a thickness of at least 0.3 cm.
63. The method of embodiment 61 or embodiment 62, wherein the heat-transfer modulating body walls are comprised of at least one layer.
64. The method of embodiment 63, wherein the thickness is adjustable by adding or removing at least one wall layer, to provide the thickness of the walls.
65. The method of embodiment 63 or embodiment 64, wherein the thermal diffusivity of the heat-transfer modulating body can be adjusted by exchanging at least one wall layer for another having a lower or higher thermal diffusivity.
66. The method of any one of embodiments 61 through 65, wherein at least a portion of the walls is pervious to the sterilant.
67. The method of any one of embodiments 60 through 66, wherein the thermal diffusivity of the heat-transfer modulating body can be adjusted by exchanging the body for another body having a lower or higher thermal diffusivity.
68. The method of any one of embodiments 35 through 67, wherein the space fully contains a process indicator.

Objects and advantages of this invention are further illustrated by the following examples, but the particular materials and amounts thereof recited in these examples, as well as other conditions and details, should not be construed to unduly limit this invention.

EXAMPLES

Example 1

Attest™ 1292 Rapid Biological Indicators (Attest BIs) and Comply™ SteriGage™ 1243 Steam Chemical Integrator (SteriGage or SG), all available from 3M Company, St. Paul, Minn., was wrapped in an absorbent paper towel and placed into three different process challenge devices fitted with two one way valves. The paper towel is commercially available as Kleenex® Premiere®, Kimberly-Clark, Roswell, Ga. The process challenge device identified as Device 2 in Tables 1-3 is illustrated in FIG. 1. The process challenge devices identified as Device 1 and Device 3 in Tables 1-3 are illustrated as in FIG. 3 which incorporates a heat-transfer modulating body. Devices 2 and 3 utilized the pivoting lid illustrated in FIGS. 1 through 3. However, the Device 1 differs from Device 3 in that the lid of Device 1 was removeable and was held in place with two screws (fasteners). The valves in Device 1 were connected to the space holding the process indicators by a channel. Devices 2 and 3 were made of ULTEM and Device 1 was made of DELRIN.

In each of the devices, one valve was oriented to open under vacuum and the other to open with pressure. Valves with opening pressures of 68.95 kPa, 96.53 kPa, and 137.9 kPa (10, 14 and 20 psi) were tested. Both valves within the prototype had the same opening or actuating pressure. The devices were exposed in a 132° C. (270° F.) 4 pulse prevacuum sterilizer, AMSCO® Eagle Model 3013 Sterilizer, Steris Corporation, Mentor, Ohio. The vacuum and pressure pulse for each cycle used a vacuum level of 20 inches of Mercury (in Hg) and a pressure pulse of 239.2 kPa (20 psig (pounds per square inch gravity)). The prototypes were tested with valves that opened at 68.95 kPa, 96.53 kPa, and 137.9 kPa (10, 14 and 20 psi).

After exposure, the SteriGage (SG) chemical integrators were read to determine if the moving front indicator dye had moved into the Reject or Accept region of the indicator. The Attest BIs were activated by crushing the inner ampules and incubating the indicators in the Attest Model 290 Autoreaders, 3M Company, St. Paul, Minn. which detects the fluorescence caused by the enzymatic breakdown of an enzyme substrate in the growth medium. After 3 hours of incubation, the Autoreader activates a green light indicating an acceptable sterilization cycle or a red light is activated to indicate a fluorescent positive indicator and a sterilization cycle failure. The indicators continued incubating for a total of 48 hours at 60° C. to allow surviving spores to grow and cause a visual color change in the growth medium from purple to yellow. The color change to yellow indicates a sterilization failure.

The prototypes assembled with the 68.95 kPa (10 psi) valves were exposed for 1, 2.5, 5 and 10 minutes and the results are shown in Table 1. The prototypes assembled with the 96.53 kPa (14 psi) valves were exposed for 5, 10, 15 and 20 minutes and the results are shown in Table 2. Table 3 shows the results for the 137.9 kPa (20 psi) valves which were exposed for 10, 15 and 20 minutes.

The data shows that as the opening pressure for the valves was increased the time required to inactivate the indicators also increased. Table 1 shows the Attest 1292 Biological Indicators in the prototypes with 68.95 kPa (10 psi) valves, were inactivated after 2.5 minutes of exposure. In Table 2, the biological indicators in devices 1 and 2 were inactivated after 10 minutes and prototype 3 required 15 minutes of exposure to inactivate the BI. The BIs in the prototypes using the 137.9 kPa (20 psi) valves required 20 minutes of exposure to inactivate the indicators. Varying the valve opening pressure is, therefore, a way to adjust the time to inactivate the indicators in the devices.

TABLE 1

| Device | Opening PSI | Exposure Time (minutes) | SteriGage | Attest 1292 3 Hour Fluorescence | Attest 1292 48 Hour Growth |
|---|---|---|---|---|---|
| 1 | 10 | 1 | Reject | + | − |
| 2 | 10 | 1 | Reject | + | + |
| 3 | 10 | 1 | Reject | + | + |
| 1 | 10 | 2.5 | Reject | − | − |
| 2 | 10 | 2.5 | Reject | − | − |
| 3 | 10 | 2.5 | Reject | − | − |
| 1 | 10 | 5 | Accept | − | − |
| 2 | 10 | 5 | Accept | − | − |
| 3 | 10 | 5 | Reject | − | − |
| 1 | 10 | 10 | Accept | − | − |
| 2 | 10 | 10 | Accept | − | − |
| 3 | 10 | 10 | Accept | − | − |

TABLE 2

| Device | Opening PSI | Exposure Time (minutes) | SteriGage | Attest 1292 3 Hour Fluorescence | Attest 1292 48 Hour Growth |
|---|---|---|---|---|---|
| 1 | 14 | 5 | Reject | + | + |
| 2 | 14 | 5 | Reject | + | + |
| 3 | 14 | 5 | Reject | + | + |
| 1 | 14 | 10 | Reject | − | − |
| 2 | 14 | 10 | Accept | − | − |
| 3 | 14 | 10 | Reject | + | + |
| 1 | 14 | 15 | Accept | − | − |
| 2 | 14 | 15 | Accept | − | − |
| 3 | 14 | 15 | Reject | − | − |
| 1 | 14 | 20 | Accept | − | − |
| 2 | 14 | 20 | Accept | − | − |
| 3 | 14 | 20 | Accept | − | − |

TABLE 3

| Device | Opening PSI | Exposure Time (minutes) | SteriGage | Attest 1292 3 Hour Fluorescence | Attest 1292 48 Hour Growth |
|---|---|---|---|---|---|
| 1 | 20 | 10 | Reject | + | + |
| 2 | 20 | 10 | Reject | + | + |
| 3 | 20 | 10 | Reject | + | + |
| 1 | 20 | 15 | Reject | + | + |
| 2 | 20 | 15 | Accept | + | + |
| 3 | 20 | 15 | Reject | + | + |
| 1 | 20 | 20 | Reject | − | − |
| 2 | 20 | 20 | Accept | − | − |
| 3 | 20 | 20 | Accept | − | − |

All references and publications or portions thereof cited herein are expressly incorporated herein by reference in their entirety into this disclosure. Exemplary embodiments of this invention are discussed and reference has been made to some possible variations within the scope of this invention. These and other variations and modifications in the invention will be apparent to those skilled in the art without departing from the scope of the invention, and it should be understood that this invention is not limited to the exemplary embodiments set forth herein. Accordingly, the invention is to be limited only by the embs provided below and equivalents thereof.

What is claimed is:

1. A device comprising:
   a container defining a space within the container, wherein the space contains a sterilization process indicator; and
   a first pressure-actuating valve associated with the container, wherein the first pressure-actuating valve regulates entrance of a sterilant into the space within the container; and
   a second pressure-actuating valve, wherein the second pressure-actuating valve regulates exiting of a gas or liquid out of the space within the container;
   wherein the device is a sterilization process challenge device.

2. The device of claim 1, wherein the first and second pressure-actuating valves are actuated when there is a pressure difference between the space within the container and outside of the container, wherein the pressure difference is at least 6.895 kPa (1 psi).

3. The device of claim 2, wherein the pressure difference at which the first and second pressure-actuating valves are actuated can be adjusted.

4. The device of claim 1, further comprising an absorbent material within the space and adjacent the process indicator when present.

5. The device of claim 1, wherein the space further contains a volume of gas of at least 5 cubic centimeters.

6. The device of claim 1, wherein the device further comprises a heat-transfer modulating body, wherein at least a portion of the body at least surrounds the process indicator when present.

7. The device of claim 6, wherein the at least a portion of the heat-transfer modulating body comprises walls which surround the indicator when present; wherein the heat-transfer modulating body walls have a thickness of at least 0.3 cm.

8. A method of determining the effectiveness of a sterilization process, the method comprising:
   providing a process challenge device of claim 1; wherein the space within the container fully contains a process indicator;
   positioning the process challenge device in a sterilization chamber;
   exposing the process challenge device to a sterilant at an elevated temperature; and
   determining whether or not the process indicator indicates that it has been exposed to sterilization process conditions effective for sterilizing an article.

9. A kit comprising at least one process challenge device of claim 1; and a plurality of sterilization process indicators for the same or different sterilization processes.

10. The kit of claim 9, further comprising a plurality of heat-transfer modulating bodies, each having the same or different thermal diffusivities and the same or different wall thicknesses and/or a plurality of process challenge devices, wherein the spaces within the containers have the same volumes or different volumes.

* * * * *